United States Patent
Dunkel et al.

(10) Patent No.: US 7,329,633 B2
(45) Date of Patent: Feb. 12, 2008

(54) DISUBSTITUTED PYRAZOLYLCARBOXANILIDES

(75) Inventors: Ralf Dunkel, Monheim (DE); Heiko Rieck, Foy-lés-Lyon (FR); Hans-Ludwig Elbe, Wuppertal (DE); Ulrike Wachendorff-Neumann, Neuwied (DE); Karl-Heinz Kuck, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 123 days.

(21) Appl. No.: 10/504,451

(22) PCT Filed: Feb. 6, 2003

(86) PCT No.: PCT/EP03/01178

§ 371 (c)(1), (2), (4) Date: Feb. 11, 2005

(87) PCT Pub. No.: WO03/070705

PCT Pub. Date: Aug. 28, 2003

(65) Prior Publication Data

US 2006/0116414 A1 Jun. 1, 2006

(30) Foreign Application Priority Data

Feb. 19, 2002 (DE) .................. 102 06 794
Apr. 8, 2002 (DE) .................. 102 15 292

(51) Int. Cl.
*A01N 43/56* (2006.01)
*C07D 231/18* (2006.01)

(52) U.S. Cl. .................. 504/280; 548/374.1

(58) Field of Classification Search ............ 548/375.1, 548/374.1; 504/280
See application file for complete search history.

(56) References Cited

U.S. PATENT DOCUMENTS

RE28,939 E    8/1976   Lafferty et al. ............ 424/273
5,330,995 A   7/1994   Eicken et al. ............... 514/355
5,480,897 A   1/1996   Eicken et al. ............... 514/365
5,556,988 A   9/1996   Eicken et al. ............ 548/374.1
5,998,450 A * 12/1999  Eicken et al. ............... 514/355

FOREIGN PATENT DOCUMENTS

| EP | 0 589 301 | 3/1994 |
| JP | 1-290662 | 11/1989 |
| JP | 9-132567 | 5/1997 |
| WO | 97/08148 | 3/1997 |
| WO | 99/09013 | 2/1999 |
| WO | 00/14071 | 3/2000 |
| WO | 01/42223 | 6/2001 |

OTHER PUBLICATIONS

Patani et al. "Bioisosterism: A Rational Approach in Drug Design" Chemical Reviews 1996, vol. 96, pp. 3147-3176.*
J. Org Chem., 66 (month unavailable) 2001, pp. 4525-4542, Chunrong Ma et al, "Efficient Asymmetric Synthesis of Biologically Important Tryptophan Analogues via a Palladium-Medicated Heteroannulation Reaction".

* cited by examiner

*Primary Examiner*—Rebecca Anderson
*Assistant Examiner*—Joseph R Kosach
(74) *Attorney, Agent, or Firm*—Richard E. L. Henderson

(57) ABSTRACT

This invention relates to novel pyrazolylcarboxanilides of formula (I)

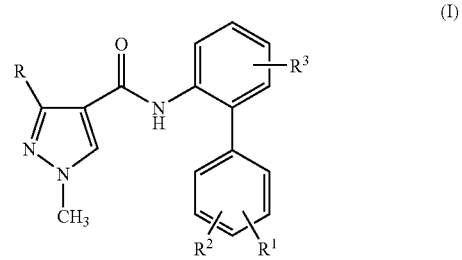

in which R, $R^1$, $R^2$ and $R^3$ are as defined in the disclosure, to a plurality of processes for preparing these substances and their use for controlling unwanted microorganisms, and to novel intermediates and their preparation.

13 Claims, No Drawings

DISUBSTITUTED PYRAZOLYLCARBOXANILIDES

The present patent application has been filed under 35 U.S.C. 371 as a national stage application of PCT/EP03/01178, filed Feb. 6, 2003, which was published in German as International Patent Publication WO 03/070705 on Aug. 28, 2003, which is entitled to the right of priority of German Patent Applications 102 06 794.5, filed Feb. 19, 2002, and 102 15 292.6, filed Apr. 8, 2002.

The present invention relates to novel pyrazolylcarboxanilides, to a plurality of processes for their preparation and to their use for controlling harmful microorganisms in crop protection and the protection of materials.

It is already known that numerous carboxanilides have fungicidal properties (cf. for example, EP 0 545 099 and JP 9132567). The activity of the substances described in these publiscation is good; however, at low application rates it is sometimes unsatisfactory.

This invention now provides novel pyrazolylcarboxanilides of the formula (I)

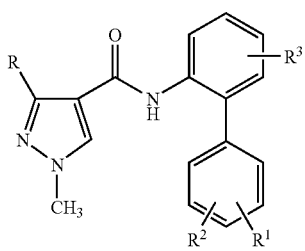
(I)

in which
R represents difluoromethyl or trifluoromethyl,
$R^1$ und $R^2$ independently of one another represent halogen, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulphonyl, $C_3$-$C_6$-cycloalkyl, or represent $C_1$-$C_4$-haloalkyl, $C_1$-$C_4$-haloalkoxy, $C_1$-$C_4$-haloalkylthio or $C_1$-$C_4$-haloalkylsulphonyl having in each case 1 to 5 halogen atoms,
$R^3$ represents fluorine.

Furthermore, it has been found that pyrazolylcarboxanilides of the formula (I) are obtained when
a) pyrazolylcarbonyl halides of the formula (II)

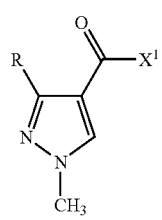
(II)

in which
R is as defined above,
$X^1$ represents halogen,
are reacted with aniline derivatives of the formula (III)

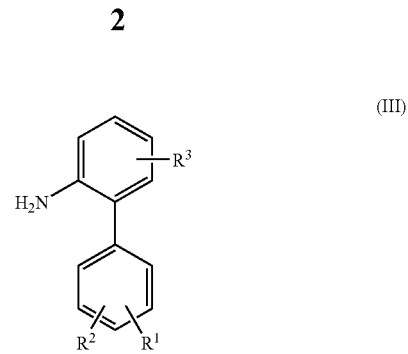
(III)

in which
$R^1$, $R^2$ and $R^3$ are as defined above,
if appropriate in the presence of an acid binder and if appropriate in the presence of a diluent, or
b) halopyrazolecarboxanilides of the formula (IV)

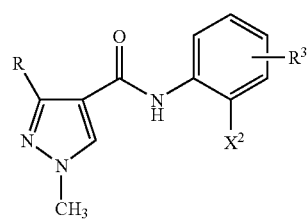
(IV)

in which
R and $R^3$ are as defined above,
$X^2$ represents bromine or iodine,
are reacted with boronic acid derivatives of the formula (V)

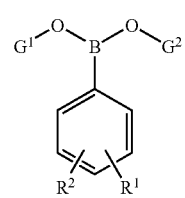
(V)

in which
$R^1$ and $R^2$ are as defined above,
$G^1$ and $G^2$ each represent hydrogen or together represent tetramethylethylene,
in the presence of a catalyst, if appropriate in the presence of an acid binder and if appropriate in the presence of a diluent, or
c) halopyrazolecarboxanilides of the formula (IV)

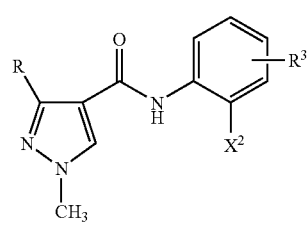
(IV)

in which

R and R³ are as defined above,

X² represents bromine or iodine, are, in a first step, reacted with a diborane derivative of the formula (VI)

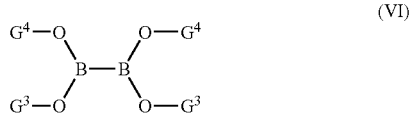

(VI)

in which

G³ and G⁴ each represent alkyl or together represent alkanediyl, in the presence of a catalyst, if appropriate in the presence of an acid binder and if appropriate in the presence of a diluent and are, without work-up, reacted in a second step with halobenzene derivatives of the formula (VII)

(VII)

in which

R¹ and R² are as defined above and

X³ represents bromine, iodine or trifluoromethylsulphonyloxy, in the presence of a catalyst, if appropriate in the presence of an acid binder and if appropriate in the presence of a diluent.

Finally, it has been found that the novel pyrazolylcarboxanilides of the formula (I) have very good microbicidal properties and can be used for controlling unwanted microorganisms both in crop protection and in the protection of materials.

Surprisingly, the pyrazolylcarboxanilides of the formula (I) according to the invention have considerably better fungicidal activity than the constitutionally most similar active compounds of the prior art having the same direction of action.

The formula (I) provides a general definition of the pyrazolylcarboxanilides according to the invention.

Preference is given to pyrazolylcarboxanilides of the formula (I), in which

R represents difluoromethyl or trifluoromethyl,

R¹ and R² independently of one another represent fluorine, chlorine, bromine, cyano, nitro, methyl, ethyl, n- or i-propyl, n-, i-, s- or t-butyl, methoxy, ethoxy, methylthio, ethylthio, n- or i-propylthio, cyclopropyl, trifluoromethyl, trichloromethyl, trifluoroethyl, difluoromethoxy, trifluoromethoxy, difluorochloromethoxy, trifluoroethoxy, difluoromethylthio, difluorochloromethylthio or trifluoromethylthio, R³ represents fluorine.

Particular preference is given to pyrazolylcarboxanilides of the formula (I), in which R represents difluoromethyl or trifluoromethyl, R¹ and R² independently of one another represent fluorine, chlorine, bromine, methyl, trifluoromethyl, difluoromethoxy or trifluoromethoxy, R³ represents fluorine.

Very particular preference is given to pyrazolylcarboxanilides of the formula (I), in which R¹ represents fluorine and R² represents chlorine.

Very particular preference is given to pyrazolylcarboxanilides of the formula (I), in which R¹ represents fluorine and R² represents fluorine.

Very particular preference is given to pyrazolylcarboxanilides of the formula (I), in which R¹ represents methyl or trifluoromethyl.

The invention preferably provides compounds of the formula (Ia),

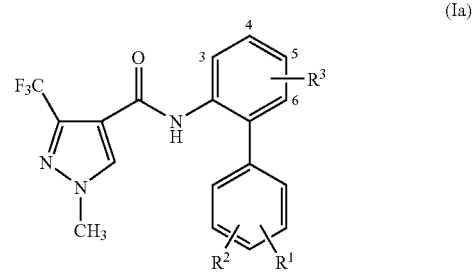

(Ia)

in which

R¹ and R² independently of one another represent fluorine, chlorine, bromine, cyano, nitro, methyl, ethyl, n- or i-propyl, n-, i-, s- or t-butyl, trifluoromethyl, trichloromethyl, trifluoroethyl, cyclopropyl, methoxy, ethoxy, difluoromethoxy, trifluoromethoxy, difluorochloromethoxy, trifluoroethoxy, methylthio, ethylthio, n- or i-propylthio, difluoromethylthio, difluorochloromethylthio, trifluoromethylthio and R³ represents fluorine.

The present invention preferably also provides compounds of the formula (Ib),

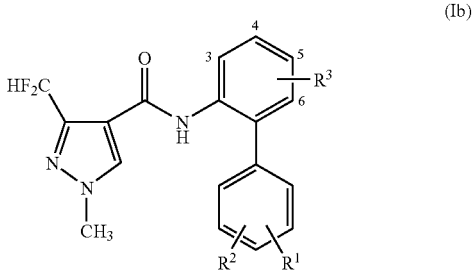

(Ib)

in which

R¹ and R² independently of one another represent fluorine, chlorine, bromine, cyano, nitro, methyl, ethyl, n- or i-propyl, n-, i-, s- or t-butyl, trifluoromethyl, trichloromethyl, trifluoroethyl, cyclopropyl, methoxy, ethoxy, difluoro-methoxy, trifluoromethoxy, difluorochloromethoxy, trifluoroethoxy, methylthio, ethylthio, n- or i-propylthio, difluoromethylthio, difluorochloromethylthio, trifluoromethylthio and $R^3$ represents fluorine.

The present application relates in particular to compounds of the formula (Ia), in which $R^1$ and $R^2$ independently of one another represent fluorine, chlorine, bromine, methyl, trifluoromethyl, difluoromethoxy or trifluoromethoxy and $R^3$ represents fluorine.

The present application relates in particular also to compounds of the formula (Ib), in which $R^1$ and $R^2$ are identical or different and independently of one another represent fluorine, chlorine, bromine, methyl, trifluoromethyl, difluoromethoxy or trifluoromethoxy and $R^3$ represents fluorine.

The present application relates very particularly preferably to compounds of the formula (Ia), in which $R^1$ and $R^2$ independently of one another represent fluorine, chlorine, bromine, methyl, trifluoromethyl, difluoromethoxy or trifluoromethoxy and $R^3$ represents 3-fluoro or 5-fluoro.

The present application relates very particularly preferably also to compounds of the formula (Ib), in which $R^1$ and $R^2$ independently of one another represent fluorine, chlorine, bromine, methyl, trifluoromethyl, difluoromethoxy or trifluoromethoxy and $R^3$ represents 3-fluoro or 5-fluoro.

Preference is furthermore given to compounds of the formula (Ic),

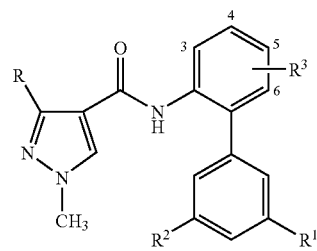

(Ic)

in which

R represents difluoromethyl or trifluoromethyl, $R^1$ and $R^2$ independently of one another represent fluorine, chlorine, bromine, cyano, nitro, methyl, ethyl, n- or i-propyl, n-, i-, s- or t-butyl, trifluoromethyl, trichloromethyl, trifluoroethyl, cyclopropyl, methoxy, ethoxy, difluoromethoxy, trifluoromethoxy, difluorochloromethoxy, trifluoroethoxy, methylthio, ethylthio, n- or i-propylthio, difluoromethylthio, difluorochloromethylthio, trifluoromethylthio and $R^3$ represents fluorine.

Preference is furthermore given to compounds of the formula (Id),

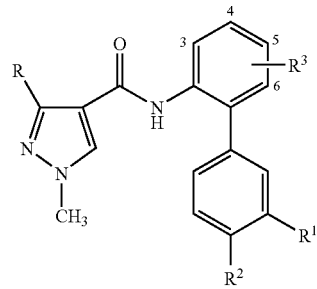

(Id)

in which

R represents difluoromethyl or trifluoromethyl, $R^1$ and $R^2$ independently of one another represent fluorine, chlorine, bromine, cyano, nitro, methyl, ethyl, n- or i-propyl, n-, i-, s- or t-butyl, trifluoromethyl, trichloromethyl, trifluoroethyl, cyclopropyl, methoxy, ethoxy, difluoromethoxy, trifluoromethoxy, difluorochloromethoxy, trifluoroethoxy, methylthio, ethylthio, n- or i-propylthio, difluoromethylthio, difluorochloromethylthio, trifluoromethylthio and $R^3$ represents fluorine.

Preference is furthermore also given to compounds of the formula (Ie), (Ie)

in which

R represents difluoromethyl or trifluoromethyl, $R^1$ and $R^2$ independently of one another represent fluorine, chlorine, bromine, cyano, nitro, methyl, ethyl, n- or i-propyl, n-, i-, s- or t-butyl, trifluoromethyl, trichloromethyl, trifluoroethyl, cyclopropyl, methoxy, ethoxy, difluoromethoxy, trifluoromethoxy, difluorochloromethoxy, trifluoroethoxy, methylthio, ethylthio, n- or i-propylthio, difluoromethylthio, difluorochloromethylthio, trifluoromethylthio and $R^3$ represents fluorine.

The present application relates in particular to compounds of the formula (Ic), in which R represents difluoromethyl or trifluoromethyl, $R^1$ and $R^2$ independently of one another represent fluorine, chlorine, bromine, methyl, trifluoromethyl, difluoromethoxy or trifluoromethoxy and $R^3$ represents fluorine.

The present application relates in particular also to compounds of the formula (Id), in which R represents difluoromethyl or trifluoromethyl, $R^1$ and $R^2$ are identical or different and independently of one another represent fluorine, chlorine, bromine, methyl, trifluoromethyl, difluoromethoxy or trifluoromethoxy and
$R^3$ represents fluorine.

The present application relates in particular also to compounds of the formula (Id), in which
R represents difluoromethyl or trifluoromethyl,
$R^1$ and $R^2$ are identical or different and independently of one another represent fluorine, chlorine, bromine, methyl, trifluoromethyl, difluoromethoxy or trifluoromethoxy and
$R^3$ represents fluorine.

The present application relates very particularly preferably to compounds of the formula (Ie), in which
R represents difluoromethyl or trifluoromethyl,
$R^1$ and $R^2$ independently of one another represent fluorine, chlorine, bromine, methyl, trifluoromethyl, difluoromethoxy or trifluoromethoxy and
$R^3$ represents 3-fluoro or 5-fluoro.

The present application relates very particularly preferably also to compounds of the formula (Id), in which
R represents difluoromethyl or trifluoromethyl,
$R^1$ and $R^2$ independently of one another represent fluorine, chlorine, bromine, methyl, trifluoromethyl, difluoromethoxy or trifluoromethoxy and
$R^3$ represents 3-fluoro or 5-fluoro.

The present application relates very particularly preferably also to compounds of the formula (Ie), in which
R represents difluoromethyl or trifluoromethyl,
$R^1$ and $R^2$ independently of one another represent fluorine, chlorine, bromine, methyl, trifluoromethyl, difluoromethoxy or trifluoromethoxy and
$R^3$ represents 3-fluoro or 5-fluoro.

The abovementioned general or preferred radical definitions or illustrations can be combined with one another as desired, i.e. including combination between the respective ranges and preferred ranges. The definitions apply both to the end products and, correspondingly, to precursors and intermediates. Moreover, some definitions may not apply.

Saturated hydrocarbon radicals such as alkyl can in each case be straight-chain or branched as far as this is possible, including in combination with heteroatoms, such as, for example, in alkoxy.

Halogen-substituted radicals, for example haloalkyl, are mono- or polyhalogenated up to the maximum possible number of substituents. In the case of polyhalogenation, the halogen atoms can be identical or different. Here, halogen represents fluorine, chlorine, bromine or iodine, in particular fluorine, chlorine or bromine.

Using, for example, 1-methyl-3-(trifluoromethyl)-1H-pyrazole-4-carbonyl chloride and 3'-chloro-4',5-difluoro-1,1'-biphenyl-2-amine as starting materials and a base, the course of the process a) according to the invention can be illustrated by the equation below:

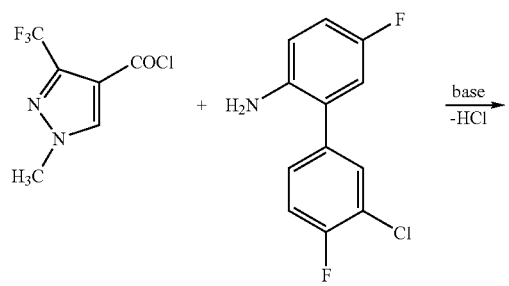

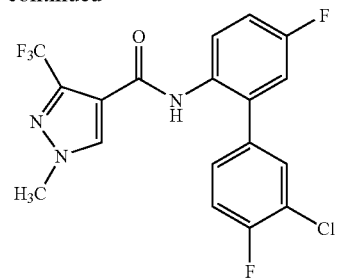

The formula (II) provides a general definition of the pyrazolylcarbonyl halides required as starting materials for carrying out process a) according to the invention. In this formula (II), R represents difluoromethyl or trifluoromethyl. $X^1$ preferably represents chlorine.

The pyrazolylcarbonyl halides of the formula (II) are known and/or can be prepared by known processes (cf., for example, JP 01290662 and U.S. Pat. No. 5,093,347).

The formula (III) provides a general definition of the aniline derivatives furthermore required as starting materials for carrying out the process a) according to the invention. In this formula (III), $R^1$, $R^2$ and $R^3$ preferably and particularly preferably have those meanings which have already been mentioned in connection with the description of the compounds of the formula (I) according to the invention as being preferred and particularly preferred for these radicals.

The aniline derivatives of the formula (III) have hitherto not been disclosed and, as novel chemical compounds, also form part of the subject-matter of the present application. They are obtained by reacting d) fluorohaloanilines of the formula (VIII)

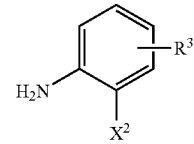

(VIII)

in which
$R^3$ and $X^2$ are as defined above,
with a boronic acid derivative of the formula (V)

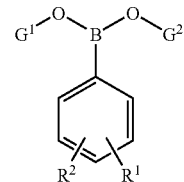

(V)

in which
$R^1$ and $R^2$ are as defined above,
$G^1$ and $G^2$ each represent hydrogen or together represent tetramethylethylene,
in the presence of a catalyst, if appropriate in the presence of an acid binder and if appropriate in the presence of a diluent.

Using, for example, 2-bromo-4-fluoroaniline and 3-chloro-4-fluorophenylboronic acid as starting materials and a base, the course of the process d) according to the invention can be illustrated by the following equation:

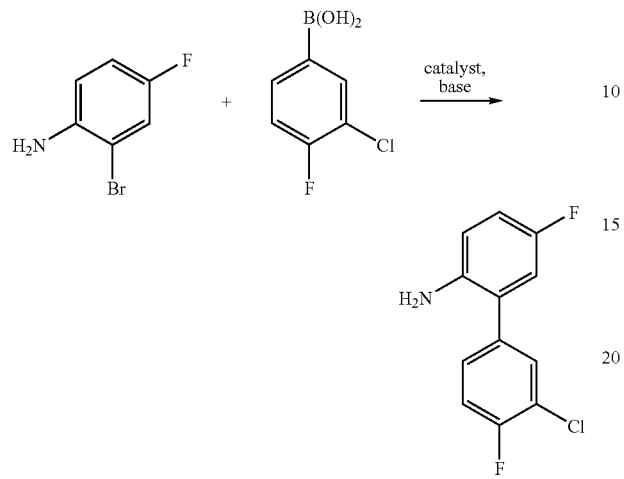

The formula (VIII) provides a general definition of the fluorohaloanilines required as starting materials for carrying out the process d) according to the invention. In this formula (VIII), $R^3$ represents fluorine and $X^2$ represents bromine or iodine.

The fluorohaloanilines of the formula (VIII) are known or can be obtained by known methods (cf., for example, U.S. Pat. No. 28,939 or J. Org. Chem. 2001, 66, 4525-4542).

The formula (V) provides a general definition of the boronic acid derivatives furthermore required as starting materials for carrying out the process d) according to the invention. In this formula (V), $R^1$ and $R^2$ preferably and particularly preferably have those meanings which have already been mentioned in connection with the description of the compounds of the formula (I) according to the invention as being preferred and particularly preferred for $R^1$ and $R^2$. $G^1$ and $G^2$ preferably each represent hydrogen or together represent tetramethylethylene.

Boronic acids of the formula (V) are known chemicals for synthesis. They can also be prepared directly, immediately prior to the reaction, from halobenzene derivatives and boronic acid esters and be reacted further without work-up.

Using N-(2-bromo-4-fluorophenyl)-1-methyl-3-(trifluoromethyl)-1H-pyrazole-4-carboxamide and 3-chloro-4-fluorophenylboronic acid as starting materials and a catalyst and a base, the course of the process b) according to the invention can be illustrated by the following equation:

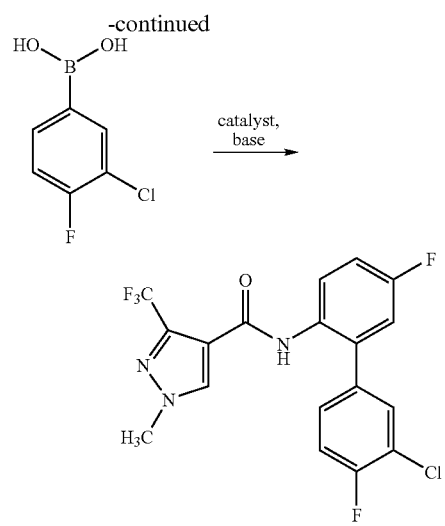

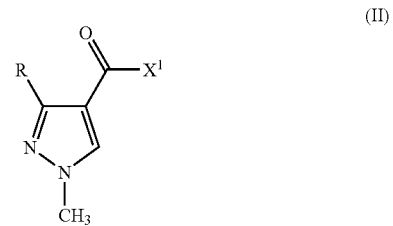

The formula (IV) provides a general definition of the halopyrazolecarboxanilides required as starting materials for carrying out the process b) according to the invention. In this formula (IV), R and $R^3$ preferably and particularly preferably have those meanings which have already been mentioned in connection with the description of the compounds of the formula (I) according to the invention as being preferred and particularly preferred for these radicals. $X^2$ preferably represents bromine or iodine.

The halopyrazolecarboxanilides of the formula (IV) have hitherto not been disclosed. They are novel chemical compounds and also form part of the subject-matter of the present application. They are obtained by reacting e) pyrazolylcarbonyl halides of the formula (II)

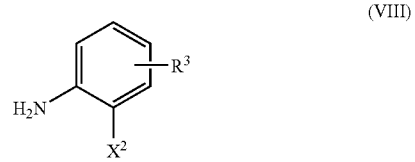

(II)

in which
R is as defined above,
$X^1$ represents halogen,
with fluorohaloanilines of the formula (VIII)

(VIII)

in which
$R^3$ and $X^2$ are as defined above,
if appropriate in the presence of an acid binder and if appropriate in the presence of a diluent.

Using, for example, 1-methyl-3-(trifluoromethyl)-1H-pyrazole-4-carbonyl chloride and 2-bromo-4-fluoroaniline as starting materials and a base, the course of the process e) according to the invention can be illustrated by the following equation:

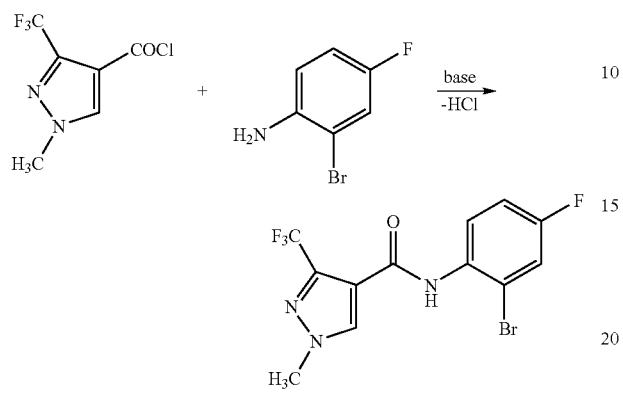

The pyrazolylcarboyl halides of the formula (II) required as starting materials for carrying out the process e) according to the invention have already been described above in connection with the process a) according to the invention.

The fluorohaloanilines of the formula (VIII) furthermore required as starting materials for carrying out the process e) according to the invention have already been described above in connection with the process d) according to the invention.

The boronic acids of the formula (V) furthermore required as starting materials for carrying out the process b) according to the invention have already been described above in connection with the process d) according to the invention.

Using, for example, N-(2-bromo-4-fluorophenyl)-1-methyl-3-(trifluoromethyl)-1H-pyrazole-4-carboxamide and 4,4,4',4',5,5,5',5'-octamethyl-2,2'-bi-1,3,2-dioxaborolane in the first step and furthermore 4-bromo-2-chloro-1-fluorobenzene in the second step as starting materials and in each step a catalyst and a base, the course of the process c) according to the invention can be illustrated by the following equation:

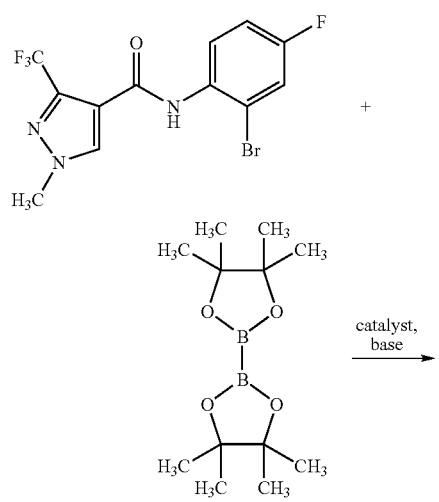

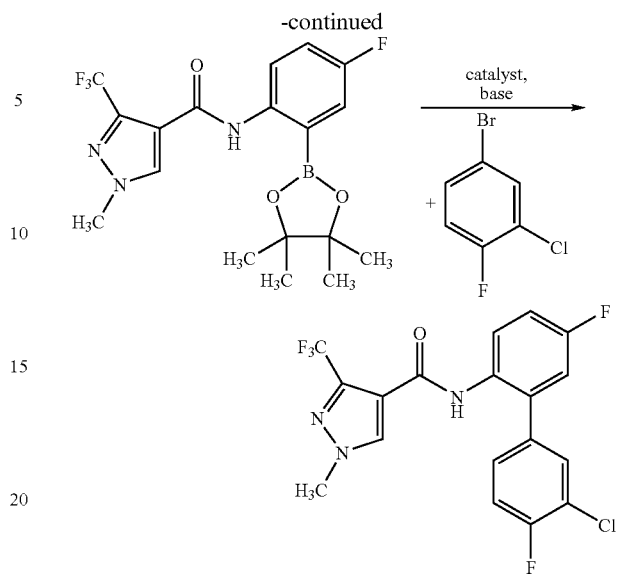

The halopyrazolecarboxanilides of the formula (IV) required as starting materials for carrying out the process c) according to the invention have already been described above in connection with the process b) according to the invention.

The formula (VI) provides a general definition of the diborane derivatives furthemore required as starting materials for carrying out the process c) according to the invention. In this formula (VI), $G^3$ and $G^4$ preferably each represent methyl, ethyl, propyl, butyl or together represent tetramethylethylene.

The diborane derivatives of the formula (VI) are generally known chemicals for synthesis.

The formula (VII) provides a general definiton of the halobenzene derivatives furthermore required as starting materials for carrying out the process c) according to the invention. In this formula (VII), $R^1$ and $R^2$ preferably and particularly preferably have those meanings which have already been mentioned in connection with the description of the compounds of the formula (I) according to the invention as being preferred and particularly preferred for these radicals. $X^3$ preferably represents bromine, iodine or trifluoromethylsulphonyloxy.

The halobenzene derivatives of the formula (VII) are generally known chemicals for synthesis.

Suitable diluents for carrying out the processes a) and e) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; or amides, such as N,N-dimethylformamide, N,N-dimethylacetamide, N-methylformanilide, N-methylpyrrolidone or hexamethylphosphoric triamide.

The processes a) and e) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the processes a) and e) according to the invention, the reaction temperatures can be varied within a relatively wide range. In general, the processes are carried out at temperatures of from 0° C. to 150° C., preferably at temperatures of from 20° C. to 110° C.

For carrying out the process a) according to the invention for preparing the compounds of the formula (I), in general from 0.2 to 5 mol, preferably from 0.5 to 2 mol, of the aniline derivative of the formula (III) are employed per mole of the pyrazolylcarbonyl halide of the formula (II).

For carrying out the process e) according to the invention for preparing the compounds of the formula (IV), in general from 0.2 to 5 mol, preferably from 0.5 to 2 mol, of fluorohaloaniline of the formula (VIII) are employed per mole of the pyrazolylcarbonyl halide of the formula (II).

Suitable diluents for carrying out the processes b), c) and d) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methyl-pyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or i-propanol, n-, i-, s- or t-butanol, ethanediol, propane-1,2-diol, ethoxyethanol, methoxyethanol, diethylene glycol monomethyl ether, diethylene glycol monoethyl ether, mixtures thereof with water or pure water.

When carrying out the processes b), c) and d) according to the invention, the reaction temperatures can be varied within a relatively wide range. In general, the processes are carried out at temperatures of from 0° C. to 150° C., preferably at temperatures of from 20° C. to 110° C.

The processes b), c) and d) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, fluorides, phosphates, carbonates or bicarbonates, such as, for example, sodium hydride, sodium amide, lithium diisopropylamide, sodium methoxide, sodium ethoxide, potassium tertbutoxide, sodium hydroxide, potassium hydroxide, sodium acetate, potassium acetate, sodium phosphate, potassium phosphate, potassium fluoride, caesium fluoride, sodium carbonate, potassium carbonate, potassium bicarbonate, sodium bicarbonate or caesium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The processes b), c) and d) according to the invention are carried out in the presence of a catalyst, such as, for example, a palladium salt or complex. Suitable for this purpose are, preferably, palladium chloride, palladium acetate, tetrakis(triphenyl-phosphine)palladium, bis(triphenylphosphine)palladium dichloride or 1,1'-bis(di-phenylphosphino)ferrocenepalladium(II) chloride.

It is also possible to generate a palladium complex in the reaction mixture by separate addition of a palladium salt and a complex ligand, such as, for example, triethyl-phosphine, tri-tert-butylphosphine, tricyclohexylphosphine, 2-(dicyclohexylphosphine)biphenyl, 2-(di-tert-butylphosphine)biphenyl, 2-(dicyclohexylphosphine)-2'-(N,N-dimethylamino)biphenyl, triphenylphosphine, tris-(o-tolyl)phosphine, sodium 3-(diphenylphosphino)benzenesulphonate, tris-2-(methoxyphenyl)-phosphine, 2,2'-bis(diphenylphosphine)-1,1'-binaphthyl, 1,4-bis(diphenylphosphine)butane, 1,2-bis(diphenylphosphine)ethane, 1,4-bis(dicyclohexylphosphine)butane, 1,2-bis(dicyclohexylphosphine)ethane, 2-(dicyclohexylphosphine)-2'-(N,N-dimethylamino)-biphenyl, bis(diphenylphosphino)ferrocene or tris-(2,4-tert-butylphenyl)phosphite to the reaction.

For carrying out the process b) according to the invention for preparing the compounds of the formula (I), in general from 1 to 15 mol, preferably from 1 to 5 mol, of the boronic acid derivative of the formula (V) are employed per mole of the halopyrazolecarboxanilide of the formula (IV).

For carrying out the process c) according to the invention for preparing the compounds of the formula (I), in general from 1 to 15 mol, preferably from 1 to 5 mol, of diborane derivative of the formula (VI) and from 1 to 15 mol, preferably from 1 to 5 mol, of halobenzene derivative of the formula (VII) are employed per mole of the halopyrazolecarboxanilide of the formula (IV).

For carrying out the process d) according to the invention for preparing the compounds of the formula (III), in general from 1 to 15 mol, preferably from 1 to 5 mol, of boronic acid derivative of the formula (V) are employed per mole of the fluorohaloaniline of the formula (VIII).

The processes a), b), c), d) and e) according to the invention are generally carried out under atmospheric pressure. However, it is also possible to operate under elevated or reduced pressure—in general between 0.1 bar and 10 bar.

The substances according to the invention have potent microbicidal activity and can be employed for controlling undesirable microorganisms, such as fungi and bacteria, in crop protection and in the protection of materials.

Fungicides can be employed in crop protection for controlling *Plasmodiophoromycetes, Oomycetes, Chytridiomycetes, Zygomycetes, Ascomycetes, Basidiomycetes* and *Deuteromycetes*.

Bactericides can be employed in crop protection for controlling *Pseudomonadaceae, Rhizobiaceae, Enterobacteriaceae, Corynebacteriaceae* and *Streptomycetaceae*.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora*;

*Pythium* species, such as, for example, *Pythium ultimum*;

*Phytophthora* species, such as, for example, *Phytophthora infestans*;

*Pseudoperonospora* species, such as, for example, *Pseudoperonospora humuli* or *Pseudoperonospora cubensis*;

*Plasmopara* species, such as, for example, *Plasmopara viticola*;

*Bremia* species, such as, for example, *Bremia lactucae*;

*Peronospora* species, such as, for example, *Peronospora pisi* or *P. brassicae*;

*Erysiphe* species, such as, for example, *Erysiphe graminis*;

*Sphaerotheca* species, such as, for example, *Sphaerotheca fuliginea*;

*Podosphaera* species, such as, for example, *Podosphaera leucotricha*;

*Venturia* species, such as, for example, *Venturia inaequalis*;

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus*;

*Puccinia* species, such as, for example, *Puccinia recondita*;

*Sclerotinia* species, such as, for example, *Sclerotinia sclerotiorum*;

*Tilletia* species, such as, for example, *Tilletia caries*;

*Ustilago* species, such as, for example, *Ustilago nuda* or *Ustilago avenae*;

*Pellicularia* species, such as, for example, *Pellicularia sasakii*;

*Pyricularia* species, such as, for example, *Pyricularia oryzae*;

*Fusarium* species, such as, for example, *Fusarium culmorum*;

*Botrytis* species, such as, for example, *Botrytis cinerea*;

*Septoria* species, such as, for example, *Septoria nodorum*;

*Leptosphaeria* species, such as, for example, *Leptosphaeria nodorum*;

*Cercospora* species, such as, for example, *Cercospora canescens*;

*Alternaria* species, such as, for example, *Alternaria brassicae*; and

*Pseudocercosporella* species, such as, for example, *Pseudocercosporella herpotrichoides*.

The active compounds according to the invention also show a strong invigorating action in plants. Accordingly, they are suitable for mobilizing the internal defences of the plant against attack by unwanted microorganisms.

In the present context, plant-invigorating (resistance-inducing) compounds are to be understood as meaning substances which are capable of stimulating the defence system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on, injecting and, in the case of propagation material, in particular in the case of seeds, furthermore by one- or multi-layer coating.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

*Alternaria,* such as *Alternaria tenuis,*
*Aspergillus,* such as *Aspergillus niger,*
*Chaetomium,* such as *Chaetomium globosum,*
*Coniophora,* such as *Coniophora puetana,*
*Lentinus,* such as *Lentinus tigrinus,*
*Penicillium,* such as *Penicillium glaucum,*
*Polyporus,* such as *Polyporus versicolor,*
*Aureobasidium,* such as *Aureobasidium pullulans,*
*Sclerophoma,* such as *Sclerophoma pityophila,*
*Trichoderma,* such as *Trichoderma viride,*
*Escherichia,* such as *Escherichia coli,*
*Pseudomonas,* such as *Pseudomonas aeruginosa,* and
*Staphylococcus,* such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:

2-phenylphenol; 8-hydroxyquinolin sulphate;

acibenzolar-S-methyl; aldimorph; amidoflumet; ampropylfos; ampropylfos-potassium; andoprim; anilazine; azaconazole; azoxystrobin;

benalaxyl; benodanil; benomyl; benthiavalicarb-isopropyl; benzamacril; benzamacrilisobutyl; bilanafos; binapacryl; biphenyl; bitertanol; blasticidin-S; bromuconazole; bupirimate; buthiobate; butylamine;

calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram;

Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon;

edifenphos; epoxiconazole; ethaboxam; ethirimol; etridiazole;

famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox;

guazatine;

hexachlorobenzene; hexaconazole; hymexazole;

imazalil; imibenconazole; iminoctadine triacetate; iminoctadine tris(albesil); iodocarb; ipconazole; iprobenfos; iprodione; iprovalicarb; irumamycin; isoprothiolane; isovaledione;

kasugamycin; kresoxim-methyl;

mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin;

natamycin; nicobifen; nitrothal-isopropyl; noviflumuron; nuarimol;

ofurace; orysastrobin; oxadixyl; oxolinic acid; oxpoconazole; oxycarboxin; oxyfenthiin;

paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine;

quinconazole; quinoxyfen; quintozene;

simeconazole; spiroxamine; sulphur;

tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole;

uniconazole;

validamycin A; vinclozolin;

zineb; ziram; zoxamide;

(2S)-N-[2-[4-[[3-(4-chlorophenyl)-2-propynyl]oxy]-3-methoxyphenyl]ethyl]-3-methyl-2-[(methylsulphonyl)amino]butanamide;

1-(1-naphthalenyl)-1H-pyrrole-2,5-dione;

2,3,5,6-tetrachloro-4-(methylsulphonyl)pyridine;

2-amino-4-methyl-N-phenyl-5-thiazolecarboxamide;

2-chloro-N-(2,3-dihydro-1,1,3-trimethyl-1H-inden-4-yl)-3-pyridinecarboxamide;

3,4,5-trichloro-2,6-pyridinedicarbonitrile;

actinovate;

cis-1-(4-chlorophenyl)-2-(1H-1,2,4-triazol-1-yl)cycloheptanol;

methyl 1-(2,3-dihydro-2,2-dimethyl-1H-inden-1-yl)-1H-imidazole-5-carboxylate;

monopotassium carbonate;

N-(6-methoxy-3-pyridinyl)-cyclopropanecarboxamide;

N-butyl-8-(1,1-dimethylethyl)-1-oxaspiro[4.5]decane-3-amine;

sodium tetrathiocarbonate;

and copper salts and preparations, such as Bordeaux mixture; copper hydroxide; copper naphthenate; copper oxychloride; copper sulphate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella,* bendiocarb, benfuracarb, bensultap, benzoximate, beta-cyfluthrin, beta-cypermethrin, bifenazate, bifenthrin, binapacryl, bioallethrin, bioallethrin-S-cyclopentylisomer, bioethanomethrin, biopermethrin, bioresmethrin, bistrifluron, BPMC, brofenprox, bromophosethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella,* cyfluthrin, cyhalofenphos, cyhexatin, cypermethrin, cyphenothrin (1R-trans-isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbaam, mesulfenfos, metaldehyde, metam-sodium, methacrifos, methamidophos, *Metharhizium anisopliae, Metharhizium flavoviride,* methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus,* parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]-octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants; such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

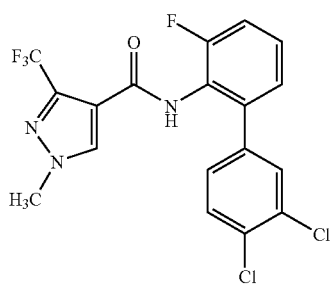

Process a)

0.333 g (1.3 mmol) of 3',4'-dichloro-3-fluoro-1,1'-biphenyl-2-amine and 0.33 g (1.56 mmol) of 1-methyl-3-(trifluoromethyl)-1H-pyrazole-4-carbonyl chloride are dissolved in 6 ml of tetrahydrofuran, and 0.36 ml (2.6 mmol) of triethylamine is added. The reaction solution is stirred at 60° C. for 16 hours. For work-up, the mixture is concentrated and the residue is chromatographed on silica gel using cyclohexane/ethyl acetate.

This gives 0.39 g (72% of theory) of N-(3',4'-dichloro-3-fluoro-1,1'-biphenyl-2-yl)-1-methyl-3-(trifluoromethyl)-1H-pyrazole-4-carboxamide of logP (pH 2.3)=3.10.

Example 2

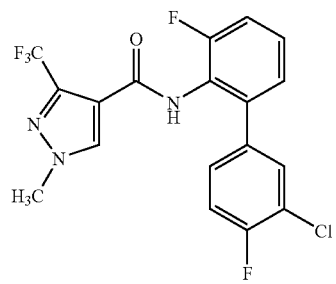

Process b)

0.256 g (0.7 mmol) of N-(2-bromo-6-fluorophenyl)-1-methyl-3-(trifluoromethyl)-1H-pyrazole-4-carboxamide and 0.12 g (0.77 mmol) of 3-chloro-4-fluorophenylboronic acid are, with exclusion of oxygen under argon, suspended in a mixture of 8 ml of toluene, 1.5 ml of ethanol and 5.25 ml of saturated sodium carbonate solution. A catalytic amount (0.01-0.3 equivalent) of tetrakis(triphenylphosphine)palladium(0) is added to the reaction mixture, and the mixture is, under argon, heated at 100° C. for one hour. The organic phase is separated off and the aqueous phase is extracted with ethyl acetate. The combined organic phases are concentrated and the residue is chromatographed on silica gel using cyclohexane/ethyl acetate (1:1).

This gives 0.27 g (96% of theory) of N-(3'-chloro-3,4'-difluoro-1,1'-biphenyl-2-yl)-1-methyl-3-(trifluoroethyl)-1H-pyrazole-4-carboxamide of logP (pH 2.3)=3.04.

The compounds of the formula (I) listed in Table 1 below are obtained analogously to Examples 1 and 2 and in accordance with what was said in the general descriptions of processes a) and b).

TABLE 1

(I)

| Ex. | R | $R^1$ | $R^2$ | $R^3$ | logP |
|---|---|---|---|---|---|
| 3 | $CF_3$ | 3'-Cl | 4'-Cl | 4-F | 3.75 |
| 4 | $CF_3$ | 3'-Cl | 4'-F | 4-F | 3.51 |
| 5 | $CF_3$ | 3'-Cl | 4'-Cl | 5-F | 3.57 |
| 6 | $CF_3$ | 3'-Cl | 4'-F | 5-F | 3.26 |
| 7 | $CHF_2$ | 3'-Cl | 4'-Cl | 3-F | 3.10 |
| 8 | $CHF_2$ | 3'-Cl | 4'-F | 3-F | 2.83 |
| 9 | $CHF_2$ | 3'-Cl | 4'-Cl | 4-F | 3.55 |
| 10 | $CHF_2$ | 3'-Cl | 4'-F | 4-F | 3.29 |
| 11 | $CHF_2$ | 3'-Cl | 4'-Cl | 5-F | 3.33 |
| 12 | $CHF_2$ | 3'-Cl | 4'-F | 5-F | 3.07 |
| 13 | $CHF_2$ | 3'-F | 5'-F | 6-F | 2.64 |

TABLE 1-continued (I)

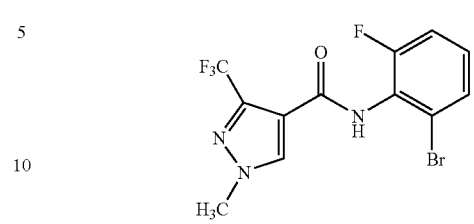

| Ex. | R | $R^1$ | $R^2$ | $R^3$ | logP |
|---|---|---|---|---|---|
| 14 | $CHF_2$ | 3'-F | 5'-F | 4-F | 3.03 |
| 15 | $CHF_2$ | 3'-F | 5'-F | 5-F | 2.81 |

Preparation of a Precursor of the Formula (III)

Example (III-1)

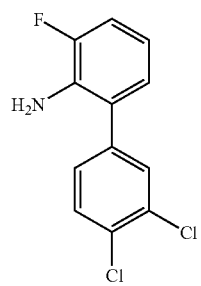

Process d)

Under exclusion of oxygen, 51.2 g (0.268 mol) of 3,4-dichlorophenylboronic acid and 42.5 g (0.223 mol) of 2-bromo-6-fluoroaniline are, under argon, suspended in a mixture of 300 ml of toluene, 30 ml of ethanol and 220 ml of saturated sodium carbonate solution. 2.6 g of tetrakis(triphenylphosphine)palladium(0) are added to the reaction mixture, and the mixture is stirred at 80° C. for 12 hours. The organic phase is removed and the aqueous phase is extracted with ethyl acetate. The combined organic phases are concentrated and the residue is chromatographed on silica gel using cyclohexane/ethyl acetate (3:1).

This gives 37.4 g (65% of theory) of 3',4'-dichloro-3-fluoro-1,1'-biphenyl-2-amine of logP (pH 2.3)=4.09.

Example (III-2)

3',4'-Dichloro-5-fluoro-1,1'-biphenyl-2-amine of logP (pH 2.3)=3.62 was obtained analogously to Example (III-1).

Preparation of the Intermediates of the Formula (IV)

Example (IV-1)

Process e)

1.0 g (5.6 mmol) of 2-bromo-6-fluoroaniline is dissolved in 5 ml of toluene, and a solution of 0.6 g (2.8 mmol) of 1-methyl-3-(trifluoromethyl)-1H-pyrazole-4-carbonyl chloride in 2 ml of toluene is added. The reaction solution is heated under reflux for 12 hours. For purification, the reaction mixture is eluted with ethyl acetate on a combined column comprising acidic anion exchanger and silica gel.

This gives 0.57 g (55.6% of theory) of N-(2-bromo-6-fluorophenyl)-1-methyl-3-(trifluoroethyl)-1H-pyrazole-4-carboxamide of logP (pH 2.3)=2.12.

The compounds of the formula (IV) listed in Table 2 below are obtained analogously to Example (IV-1) and in accordance with what was said in the general descriptions of processs e).

TABLE 2

(IV)

| Ex. | R | $R^3$ | $X^2$ | logP |
|---|---|---|---|---|
| IV-2 | $CF_3$ | 3-F | Br | 2.80 |
| IV-3 | $CF_3$ | 4-F | Br | 2.52 |
| IV-4 | $CHF_2$ | 2-F | Br | 1.89 |
| IV-5 | $CHF_2$ | 3-F | Br | 2.53 |
| IV-6 | $CHF_2$ | 4-F | Br | 2.26 |

The logP values given in the tables and Preparation Examples above are determined in accordance with EEC Directive 79/831 Annex V.A8 by HPLC (High Performance Liquid Chromatography) on a reverse-phase column (C 18). Temperature: 43° C.

In the acidic range, the determination is carried out at pH 2.3 using the mobile phases 0.1% aqueous phosphoric acid and acetonitrile; linear gradient from 10% acetonitrile to 90% acetonitrile.

Calibration is carried out using unbranched alkan-2-ones (of 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

USE EXAMPLES

Example A

*Podosphaera* Test (Apple)/Protective

| | |
|---|---|
| Solvents: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE A

*Podosphaera* test (apple)/protective

| Active compound | Application rate of active compound in g/ha | Efficacy in % |
|---|---|---|
| 1 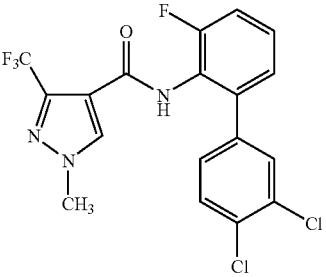 | 100 | 100 |
| 3 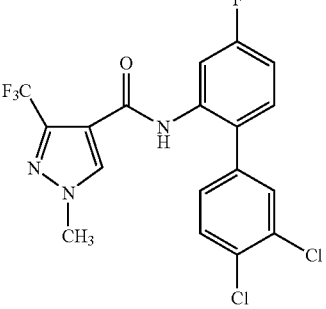 | 100 | 100 |
| 4 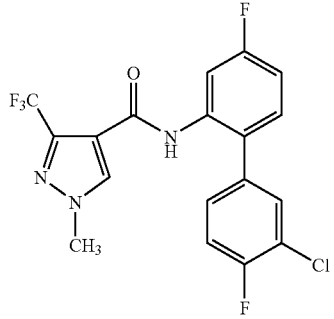 | 100 | 100 |
| 5 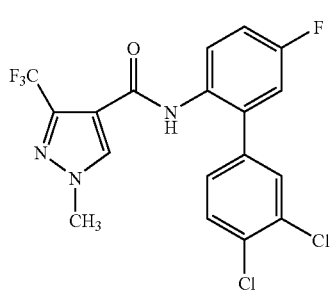 | 100 | 100 |
| 6 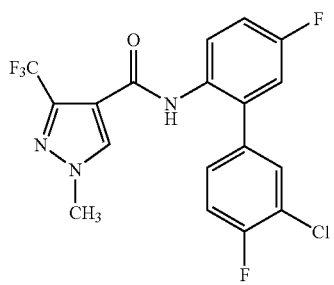 | 100 | 100 |
| 7 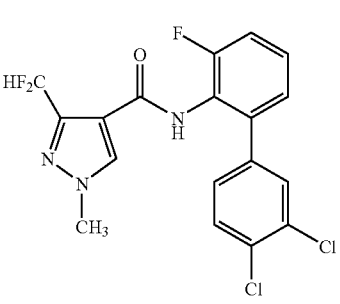 | 100 | 100 |

TABLE A-continued

Podosphaera test (apple)/protective

| Active compound | | Application rate of active compound in g/ha | Efficacy in % |
|---|---|---|---|
| 9 | HF₂C-pyrazole-C(O)NH-(biphenyl with F, Cl, Cl) | 100 | 83 |
| 10 | HF₂C-pyrazole-C(O)NH-(biphenyl with F, Cl, F) | 100 | 100 |
| 11 | HF₂C-pyrazole-C(O)NH-(biphenyl with F, Cl, Cl) | 100 | 100 |
| 12 | HF₂C-pyrazole-C(O)NH-(biphenyl with F, Cl, F) | 100 | 100 |

Example B

Sphaerotheca Test (Cucumber)/Protective

| Solvents: | 24.5 parts by weight of acetone |
|---|---|
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE B

Sphaerotheca test (cucumber)/protective

| Active compound | | Application rate of active compound in g/ha | Efficacy in % |
|---|---|---|---|
| 1 | F₃C-pyrazole-C(O)NH-(biphenyl with F, Cl, Cl) | 100 | 100 |
| 3 | F₃C-pyrazole-C(O)NH-(biphenyl with F, Cl, Cl) | 100 | 100 |

TABLE B-continued

*Sphaerotheca* test (cucumber)/protective

| Active compound | Application rate of active compound in g/ha | Efficacy in % |
|---|---|---|
| 4 | 100 | 99 |
| 5 | 100 | 100 |
| 6 | 100 | 98 |
| 7 | 100 | 100 |
| 9 | 100 | 94 |
| 10 | 100 | 100 |
| 11 | 100 | 100 |
| 12 | 100 | 100 |

Example C

*Venturia* Test (Apple)/Protective

| | |
|---|---|
| Solvents: | 24.5 parts by weight of acetone |
| | 24.5 parts by weight of dimethylacetamide |
| Emulsifier: | 1.0 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE C

*Venturia* test (apple)/protective

| Active compound | Application rate of active compound in g/ha | Efficacy in % |
|---|---|---|
| 1 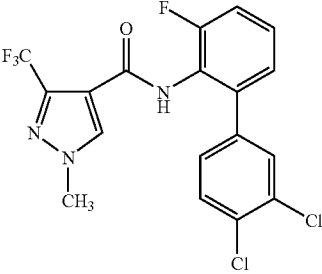 | 100 | 100 |
| 3 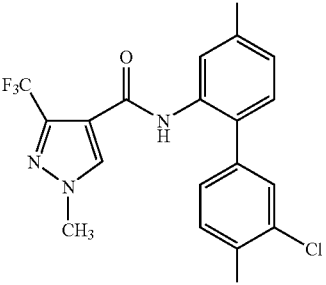 | 100 | 100 |
| 4 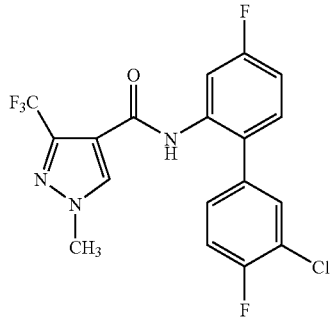 | 100 | 100 |
| 5 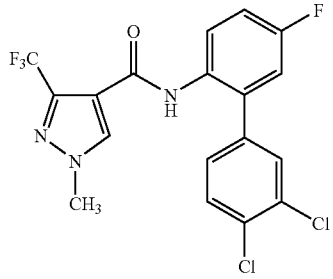 | 100 | 100 |
| 6 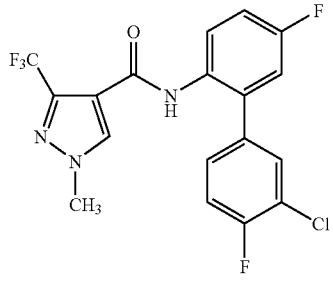 | 100 | 100 |
| 7 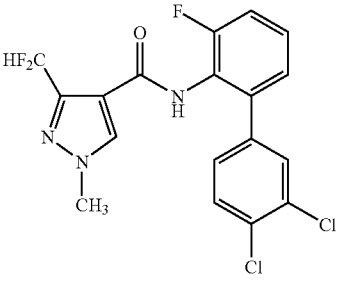 | 100 | 100 |

TABLE C-continued

Venturia test (apple)/protective

| Active compound | Application rate of active compound in g/ha | Efficacy in % |
|---|---|---|
| 9  (HF₂C-pyrazole-N(CH₃) carboxamide with 2-(3,4-dichlorophenyl)-5-fluorophenyl) | 100 | 99 |
| 10 (HF₂C-pyrazole-N(CH₃) carboxamide with 2-(3-chloro-4-fluorophenyl)-5-fluorophenyl) | 100 | 100 |
| 11 (HF₂C-pyrazole-N(CH₃) carboxamide with 2-(3,4-dichlorophenyl)-5-fluorophenyl, isomer) | 100 | 100 |
| 12 (HF₂C-pyrazole-N(CH₃) carboxamide with 2-(3-chloro-2-fluorophenyl)-5-fluorophenyl) | 100 | 100 |

Example D

Alternaria Test (Tomato)/Protective

| | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrated is diluted with water to the desired concentration.

To test for protective activity, young tomato plants are sprayed with the preparation of active compound at the stated application rate. 1 day after the treatment, the plants are inoculated with a spore suspension of *Alternaria solani* and are then kept at 100% relative atmospheric humidity and 20° C. for 24 h. The plants are then kept at 96% relative atmospheric humidity and a temperature of 20° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE D

Alternaria test (tomato)/protective

| Active compound | Application rate of active compound in g/ha | Efficacy in % |
|---|---|---|
| 1 (F₃C-pyrazole-N(CH₃) carboxamide with 2-(3,4-dichlorophenyl)-6-fluorophenyl) | 750 | 100 |
| 2 (F₃C-pyrazole-N(CH₃) carboxamide with 2-(3-chloro-4-fluorophenyl)-6-fluorophenyl) | 750 | 100 |

TABLE D-continued

*Alternaria* test (tomato)/protective

| Active compound | Application rate of active compound in g/ha | Efficacy in % |
|---|---|---|
| 3 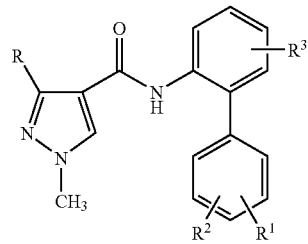 | 750 | 100 |
| 4 | 750 | 100 |
| 5 | 750 | 100 |
| 6 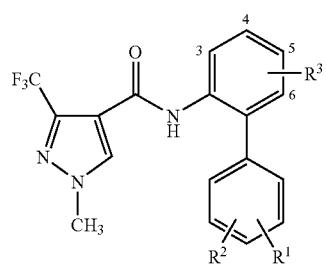 | 750 | 100 |

What is claimed is:

1. A pyrazolylcarboxanilide of formula (I)

(I)

in which
R represents difluoromethyl or trifluoromethyl,
$R^1$ and $R^2$ independently of one another represent chlorine, bromine, cyano, nitro, $C_1$-$C_6$-alkyl, $C_2$-$C_6$-alkenyl, $C_1$-$C_4$-alkoxy, $C_1$-$C_4$-alkylthio, $C_1$-$C_4$-alkylsulphonyl, or $C_3$-$C_6$-cycloalkyl; or represent $C_1$-$C_4$-haloalkyl, $C_1$-$C_4$-haloalkoxy, $C_1$-$C_4$-haloalkylthio, or $C_1$-$C_4$-haloalkylsulphonyl having in each case 1 to 5 halogen atoms, and
$R^3$ represents fluorine.

2. A pyrazolylcarboxanilide of formula (I) according to claim 1 in which
R represents difluoromethyl or trifluoromethyl,
$R^1$ and $R^2$ independently of one another represent chlorine, bromine, cyano, nitro, methyl, ethyl, n- or i-propyl, n-, i-, s-, or t-butyl, methoxy, ethoxy, methylthio, ethylthio, n- or i-propylth io, cyclopropyl, trifluoromethyl, trichloromethyl, trifluoroethyl, difluoromethoxy, trifluoromethoxy, difluorochloromethoxy, trifluoroethoxy, difluoromethylthio, difluoroch loromethylthio, or trifluoromethylthio, and
$R^3$ represents fluorine.

3. A pyrazolylcarboxanilide of formula (I) according to claim 1 in which
R represents difluoromethyl or trifluoromethyl,
$R^1$ and $R^2$ independently of one another represent chlorine, bromine, methyl, trifluoromethyl, difluoromethoxy, or trifluoromethoxy, and
$R^3$ represents fluorine.

4. A pyrazolylcarboxanilide of formula (I) according to claim 1 in which $R^1$ represents methyl or trifluoromethyl.

5. A compound of formula (Ia)

(Ia)

in which
$R^1$ and $R^2$ independently of one another represent chlorine, bromine, cyano, nitro, methyl, ethyl, n- or i-propyl, n-, i-, s-, or t-butyl, trifluoromethyl, trichloromethyl, trifluoroethyl, cyclopropyl, methoxy, ethoxy, difluoromethoxy, trifluoromethoxy, difluorochloromethoxy, trifluoroethoxy, methylthio, ethylthio, n- or i-propylthio, difluoromethylthio, difluorochloromethylthio, or trifluoromethylthio, and R³ represents fluorine.

6. A compound of formula (Ib)

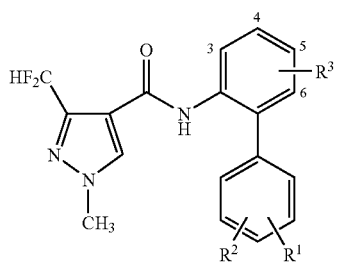

(Ib)

in which

R¹ and R² independently of one another represent chlorine, bromine, cyano, nitro, methyl, ethyl, n- or i-propyl, n-, i-, s-, or t-butyl, trifluoromethyl, trichloromethyl, trifluoroethyl, cyclopropyl, methoxy, ethoxy, difluoromethoxy, trifluoromethoxy, difluorochloromethoxy, trifluoroethoxy, methylthio, ethylthio, n- or i-propylthio, difluoromethylthio, difluorochloromethylthio, or trifluoromethylthio, and R³ represents fluorine.

7. A compound of formula (Ic)

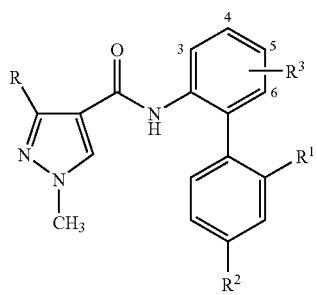

(Ic)

in which

R represents difluoromethyl or trifluoromethyl,

R¹ and R² independently of one another represent chlorine, bromine, cyano, nitro, methyl, ethyl, n- or i-propyl, n-, i-, s-, or t-butyl, trifluoromethyl, trichloromethyl, trifluoroethyl, cyclopropyl, methoxy, ethoxy, difluoromethoxy, trifluoromethoxy, difluorochloromethoxy, trifluoroethoxy, methylthio, ethylthio, n- or i-propylthio, difluoromethylthio, difluorochloromethylthio, or trifluoromethylthio, and R³ represents fluorine.

8. A compound of formula (Id)

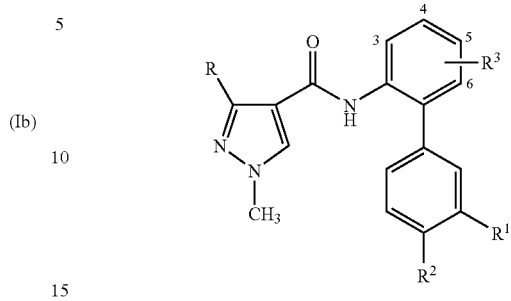

(Id)

in which

R represents difluoromethyl or trifluoromethyl,

R¹ and R² independently of one another represent chlorine, bromine, cyano, nitro, methyl, ethyl, n- or i-propyl, n-, i-, s-, or t-butyl, trifluoromethyl, trichloromethyl, trifluoroethyl, cyclopropyl, methoxy, ethoxy, difluoromethoxy, trifluoromethoxy, difluorochloromethoxy, trifluoroethoxy, methylthio, ethylthio, n- or i-propylthio, difluoromethylthio, difluorochloromethylthio, or trifluoromethylthio, and R³ represents fluorine.

9. A compound of formula (Ie)

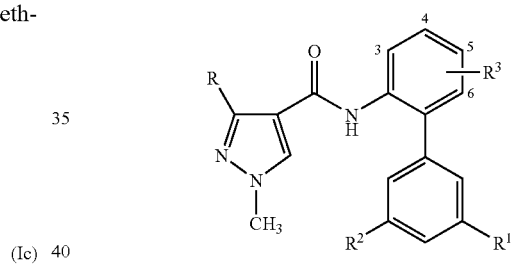

(Ie)

in which

R represents difluoromethyl or trifluoromethyl,

R¹ and R² independently of one another represent chlorine, bromine, cyano, nitro, methyl, ethyl, n- or i-propyl, n-, i-, s-, or t-butyl, trifluoromethyl, trichloromethyl, trifluoroethyl, cyclopropyl, methoxy, ethoxy, difluoromethoxy, trifluoromethoxy, difluorochloromethoxy, trifluoroethoxy, methylthio, ethylthio, n- or i-propylthio, difluoromethylthio, difluorochloromethylthio, or trifluoromethylthio, and R³ represents fluorine.

10. A process for preparing a pyrazolylcarboxanilide of formula (I) according to claim 1 comprising (a) reacting a pyrazolylcarbonyl halide of formula (II)

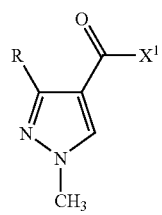

(II)

in which
R is as defined for formula (I) in claim 1, and
$X^1$ represents halogen,
with an aniline derivative of formula (III)

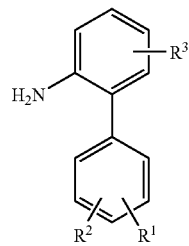

(III)

in which $R^1$, $R^2$, and $R^3$ are as defined for formula (I) in claim 1, optionally in the presence of an acid binder and optionally in the presence of a diluent, or (b) reacting a halopyrazolecarboxanilide of formula (IV)

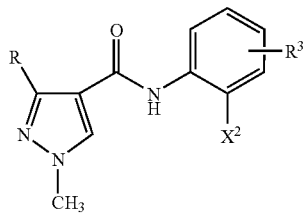

(IV)

in which
R and $R^3$ are as defined for formula (I) in claim 1, and
$X^2$ represents bromine or iodine,
with a boronic acid derivative of formula (V)

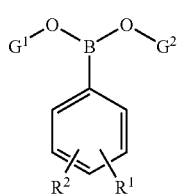

(V)

in which
$R^1$ and $R^2$ are as defined for formula (I) in claim 1, and
$G^1$ and $G^2$ each represent hydrogen or together represent tetramethylethylene,
in the presence of a catalyst, optionally in the presence of an acid binder, and optionally in the presence of a diluent, or (c) reacting In a first step a halopyrazolecarboxanillde of formula (IV)

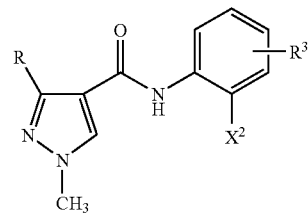

(IV)

in which
R and $R^3$ are defined for formula (I) in claim 1, and
$X^2$ represents bromine or iodine,
with a diborane derivative of formula (VI)

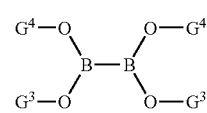

(VI)

in which $G^3$ and $G^4$ each represent alkyl or together represent alkanedlyl,
in the presence of a catalyst, optionally in the presence of an acid binder, and optionally in the presence of a diluent, and
reacing without work-up in a second step with a haiobenzene derivative of the formula (VII)

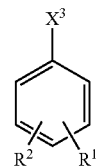

(VII)

in which
$R^1$ and $R^2$ are as defined for formula (I) in claim 1, and
$X^3$ represents bromine, iodine, or trifluoromethylsulphonyloxy,
in the presence of a catalyst, optionally in the presence of an acid binder, and optionally in the presence of a diluent.

11. A composition comprising one or more pyrazolylcarboxanilides of formula (I) according to claim 1 and one or more extenders and/or surfactants.

12. A method for controlling unwanted fungi comprising applying an effective amount of a pyrazolylcarboxanilide of formula (I) according to claim 1 to the fungi and/or their habitat.

13. A process for preparing a composition comprising mixing a pyrazolylcarboxanilide of formula (I) according to claim 1 with one or more extenders and/or surfactants.

* * * * *